United States Patent
Vasily (10) Patent No.: US 7,029,469 B2
(45) Date of Patent: *Apr. 18, 2006

(54) METHOD AND APPARATUS FOR LASER REMOVAL OF HAIR

(75) Inventor: David B. Vasily, Bethlehem, PA (US)

(73) Assignee: Palomar Medical Technologies, Inc., Burlington, MA (US)

(*) Notice: Subject to any disclaimer, the term of this patent is extended or adjusted under 35 U.S.C. 154(b) by 38 days.

This patent is subject to a terminal disclaimer.

(21) Appl. No.: 10/358,078

(22) Filed: Feb. 4, 2003

(65) Prior Publication Data

US 2004/0015156 A1  Jan. 22, 2004

Related U.S. Application Data

(63) Continuation-in-part of application No. 09/394,171, filed on Sep. 13, 1999, now Pat. No. 6,514,242.

(60) Provisional application No. 60/110,732, filed on Dec. 3, 1998.

(51) Int. Cl.
*A61B 18/18* (2006.01)

(52) U.S. Cl. .................. 606/9; 606/3; 606/10; 606/12; 600/306; 600/310; 128/898

(58) Field of Classification Search .............. 606/3, 606/8–13, 127; 600/306, 310; 607/88, 89; 128/898
See application file for complete search history.

(56) References Cited

U.S. PATENT DOCUMENTS

| 3,327,712 A | 6/1967 | Kaufman et al. |
| 3,527,932 A | 9/1970 | Thomas |
| 3,538,919 A | 11/1970 | Meyer |
| 3,622,743 A | 11/1971 | Muncheryan |
| 3,693,623 A | 9/1972 | Harte et al. |
| 3,818,914 A | 6/1974 | Bender |
| 3,834,391 A | 9/1974 | Block |
| 3,900,034 A | 8/1975 | Katz et al. |
| 4,233,493 A | 11/1980 | Nath |
| 4,273,109 A | 6/1981 | Enderby |
| 4,316,467 A | 2/1982 | Muckerheide |
| 4,388,924 A | 6/1983 | Weissman et al. |
| 4,461,294 A | 7/1984 | Baron |

(Continued)

FOREIGN PATENT DOCUMENTS

AT    400305 B    4/1995

(Continued)

OTHER PUBLICATIONS

G.B. Altshuler et al., "Acoustic response of hard dental tissues to pulsed laser action," SPIE, vol. 2080, Dental Application of Lasers, pp. 97-103, 1993.

(Continued)

*Primary Examiner*—A. Farah (74) *Attorney, Agent, or Firm*—Thomas J. Engellenner; Deborah A. Miller; Nutter McClennen & Fish LLP (57) ABSTRACT

A method and apparatus for removing hairs from living skin is provided involving the measurement with a colorimeter of the color of the area of the skin where the hair is to be removed to obtain a representative color value, employing the color value to select an optimum range of laser energy necessary to inactivate hair follicles in the area, yet minimize any inflammatory reaction, and directing laser energy of optimum range at the skin area to depilate such area.

8 Claims, 1 Drawing Sheet

U.S. PATENT DOCUMENTS

| | | |
|---|---|---|
| 4,539,987 A | 9/1985 | Nath et al. |
| 4,608,978 A | 9/1986 | Rohr |
| 4,617,926 A | 10/1986 | Sutton |
| 4,695,697 A | 9/1987 | Kosa |
| 4,718,416 A | 1/1988 | Nanaumi |
| 4,733,660 A | 3/1988 | Itzkan |
| 4,747,660 A | 5/1988 | Nishioka et al. |
| 4,819,669 A | 4/1989 | Politzer |
| 4,832,024 A | 5/1989 | Boussignac et al. |
| 4,860,172 A | 8/1989 | Schlager et al. |
| 4,860,744 A | 8/1989 | Johnson et al. |
| 4,917,084 A | 4/1990 | Sinofsky |
| 4,926,227 A | 5/1990 | Jensen |
| 4,945,239 A | 7/1990 | Wist et al. |
| 5,000,752 A | 3/1991 | Hoskin et al. |
| 5,057,104 A | 10/1991 | Chess |
| 5,059,192 A | 10/1991 | Zaias |
| 5,065,515 A | 11/1991 | Iderosa |
| 5,071,417 A | 12/1991 | Sinofsky |
| 5,108,388 A | 4/1992 | Trokel |
| 5,137,530 A | 8/1992 | Sand |
| 5,140,984 A | 8/1992 | Dew et al. |
| 5,178,617 A | 1/1993 | Kuizenga et al. |
| 5,182,557 A | 1/1993 | Lang |
| 5,182,857 A | 2/1993 | Simon |
| 5,196,004 A | 3/1993 | Sinofsky |
| 5,207,671 A | 5/1993 | Franken et al. |
| 5,225,926 A | 7/1993 | Cuomo et al. |
| 5,226,907 A | 7/1993 | Tankovich |
| 5,282,797 A | 2/1994 | Chess |
| 5,300,097 A | 4/1994 | Lerner et al. |
| 5,304,170 A | 4/1994 | Green |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,344,418 A | 9/1994 | Ghaffari |
| 5,344,434 A | 9/1994 | Talmore |
| 5,348,551 A | 9/1994 | Spears et al. |
| 5,350,376 A | 9/1994 | Brown |
| 5,380,317 A | 1/1995 | Everett et al. |
| 5,403,306 A | 4/1995 | Edwards et al. |
| 5,405,368 A | 4/1995 | Eckhouse |
| 5,415,654 A | 5/1995 | Daikuzono |
| 5,425,728 A | 6/1995 | Tankovich |
| 5,474,549 A | 12/1995 | Ortiz et al. |
| 5,486,172 A | 1/1996 | Chess |
| 5,505,726 A | 4/1996 | Meserol |
| 5,505,727 A | 4/1996 | Keller |
| 5,519,534 A | 5/1996 | Smith et al. |
| 5,522,813 A | 6/1996 | Trelles |
| 5,531,739 A | 7/1996 | Trelles |
| 5,558,667 A | 9/1996 | Yarborough et al. |
| 5,578,866 A | 11/1996 | DePoorter et al. |
| 5,595,568 A | 1/1997 | Anderson et al. |
| 5,616,140 A | 4/1997 | Prescott |
| 5,620,478 A | 4/1997 | Eckhouse |
| 5,626,631 A | 5/1997 | Eckhouse |
| 5,630,811 A | 5/1997 | Miller |
| 5,649,972 A | 7/1997 | Hochstein |
| 5,655,547 A | 8/1997 | Karni |
| 5,658,323 A | 8/1997 | Miller |
| 5,662,643 A | 9/1997 | Kung et al. |
| 5,662,644 A | 9/1997 | Swor |
| 5,683,380 A | 11/1997 | Eckhouse et al. |
| 5,698,866 A | 12/1997 | Doiron et al. |
| 5,707,403 A | 1/1998 | Grove et al. |
| 5,720,772 A | 2/1998 | Eckhouse |
| 5,735,844 A | 4/1998 | Anderson et al. |
| 5,735,884 A | 4/1998 | Thompson et al. |
| 5,743,901 A | 4/1998 | Grove et al. |
| 5,755,751 A | 5/1998 | Eckhouse |
| 5,759,200 A | 6/1998 | Azar |
| 5,782,249 A | 7/1998 | Weber et al. |
| 5,810,801 A | 9/1998 | Anderson et al. |
| 5,817,089 A | 10/1998 | Tankovich et al. |
| 5,820,625 A | 10/1998 | Izawa et al. |
| 5,820,626 A | 10/1998 | Baumgardner |
| 5,824,023 A | 10/1998 | Anderson |
| 5,828,803 A | 10/1998 | Eckhouse |
| 5,830,208 A | 11/1998 | Muller |
| 5,836,999 A | 11/1998 | Eckhouse et al. |
| 5,840,048 A | 11/1998 | Cheng |
| 5,849,029 A | 12/1998 | Eckhouse et al. |
| 5,853,407 A | 12/1998 | Miller |
| 5,885,211 A | 3/1999 | Eppstein et al. |
| 5,885,273 A | 3/1999 | Eckhouse et al. |
| 5,885,274 A | 3/1999 | Fullmer et al. |
| 5,891,063 A | 4/1999 | Vigil |
| 5,944,748 A | 8/1999 | Mager et al. |
| 5,948,011 A | 9/1999 | Knowlton |
| 5,954,710 A | 9/1999 | Paolini et al. |
| 5,964,749 A | 10/1999 | Eckhouse et al. |
| 5,968,033 A | 10/1999 | Fuller |
| 5,968,034 A | 10/1999 | Fullmer et al. |
| 6,015,404 A | 1/2000 | Altshuler et al. |
| 6,027,495 A | 2/2000 | Miller |
| RE36,634 E | 3/2000 | Ghaffari |
| 6,050,990 A | 4/2000 | Tankovich et al. |
| 6,056,738 A | 5/2000 | Marchitto et al. |
| 6,059,820 A | 5/2000 | Baronov |
| 6,074,382 A | 6/2000 | Asah et al. |
| 6,080,146 A | 6/2000 | Altshuler et al. |
| 6,096,029 A | 8/2000 | O'Donnell, Jr. |
| 6,096,209 A | 8/2000 | O'Brien et al. |
| 6,104,959 A | 8/2000 | Spertell |
| 6,120,497 A | 9/2000 | Anderson |
| 6,149,644 A | 11/2000 | Xie |
| 6,168,589 B1 * | 1/2001 | Tobinick .................. 606/9 |
| 6,174,325 B1 | 1/2001 | Eckhouse |
| 6,197,020 B1 | 3/2001 | O'Donnell |
| 6,235,016 B1 | 5/2001 | Stewart |
| 6,267,780 B1 | 7/2001 | Streeter |
| 6,273,884 B1 | 8/2001 | Altshuler et al. |
| 6,273,885 B1 | 8/2001 | Koop et al. |
| 6,280,438 B1 | 8/2001 | Eckhouse et al. |
| 6,306,130 B1 | 10/2001 | Anderson et al. |
| 6,308,088 B1 * | 10/2001 | MacFarlane et al. ........ 600/310 |
| 6,354,370 B1 | 3/2002 | Miller et al. |
| 6,471,712 B1 | 10/2002 | Burres |
| 6,475,211 B1 | 11/2002 | Chess et al. |
| 6,508,813 B1 | 1/2003 | Altshuler |
| 6,511,475 B1 | 1/2003 | Altshuler et al. |
| 6,514,242 B1 * | 2/2003 | Vasily et al. .................. 606/9 |
| 6,517,532 B1 | 2/2003 | Altshuler et al. |
| 6,605,080 B1 | 8/2003 | Altshuler et al. |
| 6,648,904 B1 | 11/2003 | Altshuler et al. |

FOREIGN PATENT DOCUMENTS

| | | |
|---|---|---|
| AU | 1851583 A | 3/1984 |
| DE | 3837248 A1 | 5/1990 |
| EP | 0142671 A1 | 5/1985 |
| EP | 0565331 A2 | 10/1993 |
| EP | 0598984 A1 | 6/1994 |
| EP | 0724894 A2 | 8/1996 |
| EP | 0726083 A2 | 8/1996 |
| EP | 0736308 A2 | 10/1996 |
| EP | 0755698 A2 | 1/1997 |
| EP | 0763371 A2 | 3/1997 |
| EP | 0765673 A2 | 4/1997 |
| EP | 0765674 A2 | 4/1997 |
| EP | 0783904 A2 | 7/1997 |
| EP | 1038505 A2 | 9/2000 |

| | | | |
|---|---|---|---|
| EP | 1219258 A1 | 7/2002 |
| FR | 2199453 | 4/1974 |
| FR | 2591902 | 6/1987 |
| GB | 2044908 A | 10/1980 |
| GB | 2123287 A | 2/1984 |
| GB | 2360946 A | 10/2001 |
| RU | 2082337 C1 | 6/1997 |
| RU | 2089126 C1 | 10/1997 |
| RU | 2089127 C1 | 10/1997 |
| RU | 2096051 C1 | 11/1997 |
| RU | 2122848 C1 | 10/1998 |
| WO | WO 86/02783 | 5/1986 |
| WO | WO 90/00420 | 1/1990 |
| WO | WO 92/16338 | 1/1992 |
| WO | WO 92/19165 | 11/1992 |
| WO | WO 93/05920 | 4/1993 |
| WO | WO 95/15725 | 6/1995 |
| WO | WO 95/32441 | 11/1995 |
| WO | WO 96/23447 | 8/1996 |
| WO | WO 96/25979 | 8/1996 |
| WO | WO 97/13458 | 4/1997 |
| WO | WO 98/04317 | 2/1998 |
| WO | WO 98/24507 | 6/1998 |
| WO | WO 98/51235 | 11/1998 |
| WO | WO 98/52481 | 11/1998 |
| WO | WO 99/27997 A1 | 6/1999 |
| WO | WO 99/29243 | 6/1999 |
| WO | WO 99/38569 | 8/1999 |
| WO | WO 99/46005 | 9/1999 |
| WO | WO 99/49937 A1 | 10/1999 |
| WO | WO 00/03257 | 1/2000 |
| WO | WO 00/71045 A1 | 11/2000 |
| WO | WO 00/74781 A1 | 12/2000 |
| WO | WO 00/78242 A1 | 12/2000 |
| WO | WO 01/03257 A1 | 1/2001 |
| WO | WO 01/34048 A1 | 5/2001 |
| WO | WO 01/42671 A1 | 6/2001 |
| WO | WO 01/54606 A1 | 8/2001 |
| WO | WO 02/53050 A1 | 7/2002 |
| WO | WO 02/094116 A1 | 11/2002 |

OTHER PUBLICATIONS

G.B. Altshuler et al., "Extended theory of selective photothermolysis," Lasers in Surgery and Medicine, vol. 29, pp. 416-432, 2001.

R.L. Amy & R. Storb, "Selective mitochondrial damage by a ruby laser microbeam: An electron microscopic study," Science, vol. 15, pp. 756-758, Nov. 1965.

R.R. Anderson et al., "The optics of human skin," Journal of Investigative Dermatology, vol. 77, No. 1, pp. 13-19, 1981.

R.R. Anderson & J.A. Parrish, "Selective photothermolysis: Precise microsurgery by selective absorption of pulsed radiation," Science, vol. 220, pp. 524-527, Apr. 1983.

A.V. Belikov et al., "Identification of enamel and dentine under tooth laser treatment," SPIE vol. 2623, Progress in Biomedical Optics Europe Series, Proceedings of Medical Applications of Lasers III, pp. 109-116, Sep. 1995.

P. Bjerring et al., "Selective Non-Ablative Wrinkle Reduction by Laser," J Cutan Laser Ther, vol. 2, pp. 9-15, 2000.

J.S. Dover et al., "Pigmented guinea pig skin irradiated with Q-switched ruby laser pulses," Arch Dermatol, vol. 125, pp. 43-49, Jan. 1989.

L.H. Finkelstein & L.M. Blatstein, "Epilation of hair-bearing urethral grafts using the neodyminum:yag surgical laser," Journal of Urology, vol. 146, pp. 840-842, Sep. 1991.

L. Goldman, Biomedical Aspects of the Laser, Springer-Verlag New York Inc., publishers, Chapts. 1, 2, & 23, 1967.

L. Goldman, "Dermatologic manifestations of laser radiation," Proceedings of the First Annual Conference on Biologic Effects of Laser Radiation, Federation of American Societies for Experimental Biology, Supp. No. 14, pp. S-92-S-93, Jan.-Feb. 1965.

L. Goldman, "Effects of new laser systems on the skin," Arch Dermatol., vol. 108, pp. 385-390, Sep. 1973.

L. Goldman, "Laser surgery for skin cancer," New York State Journal of Medicine, pp. 1897-1900, Oct. 1977.

L. Goldman, "Surgery by laser for malignant melanoma," J. Dermatol. Surg. Oncol., vol., 5, No. 2, pp. 141-144, Feb. 1979.

L. Goldman, "The skin," Arch Environ Health, vol. 18, pp. 434-436, Mar. 1969.

L. Goldman & D.F. Richfield, "The effect of repeated exposures to laser beams," Acta derm.—vernereol., vol. 44, pp. 264-268, 1964.

L. Goldman & R.J. Rockwell, "Laser action at the cellular level," JAMA, vol. 198, No. 6, pp. 641-644, Nov. 1966.

L. Goldman & R.G. Wilson, "Treatment of basal cell epithelioma by laser radiation," JAMA, vol. 189, No. 10, pp. 773-775.

L. Goldman et al., The biomedical aspects of lasers, JAMA, vol. 188, No. 3, pp. 302-306, Apr. 1964.

L. Goldman et al., "Effect of the laser beam on the skin, Preliminary report" Journal of Investigative Dermatology, vol. 40, pp. 121-122, 1963.

L. Goldman et al., "Effect of the laser beam on the skin, III. Exposure of cytological preparations," Journal of Investigative Dermatology, vol. 42, pp. 247-251, 1964.

L. Goldman et al., "Impact of the laser on nevi and melanomas," Archives of Dermatology, vol. 90, pp. 71-75, Jul. 1964.

L. Goldman et al., "Laser treatment of tattoos, A preliminary survey of three year's clinical experience," JAMA, vol. 201, No. 11, pp. 841-844, Sep. 1967.

L. Goldman et al., "Long-term laser exposure of a senile freckle," ArchEnviron Health, vol. 22, pp. 401-403, Mar. 1971.

L. Goldman et al., "Pathology, Pathology of the effect of the laser beam on the skin," Nature, vol. 197, No. 4870, pp. 912-914, Mar. 1963.

L. Goldman et al., "Preliminary investigation of fat embolization from pulsed ruby laser impacts of bone," Nature, vol. 221, pp. 361-363, Jan. 1969.

L. Goldman et al., "Radiation from a Q-switched ruby laser, Effect of repeated impacts of power output of 10 megawatts on a tattoo of man," Journal of Investigative Dermatology, vol. 44, pp. 69-71, 1965.

L. Goldman et al., "Replica microscopy and scanning electron microscopy of laser impacts on the skin," Journal of Investigative Dermatology, vol. 52, No. 1, pp. 18-24, 1969.

M.C. Grossman et al., "Damage to hair follicles by normal-mode ruby laser pulses," Journal of he American Academy of Dermatology, vol. 35, No. 6, pp. 889-894, Dec. 1996.

E. Klein et al., "Biological effects of laser radiation 1., "Northeast Electroncis Research and Engineering Meeting, NEREM Record, IEEE catalogue No. F-60, pp. 108-109, 1965.

J.G. Kuhns et al., "Laser injury in skin," Laboratory Investigation, vol. 17, No. 1, pp. 1-13, Jul. 1967.

J.G. Kuhns et al., "Biological effects of laser radiation II Effects of laser irradiation on the skin," NEREM Record, pp. 152-153, 1965.

R.J. Margolis et al., "Visible action spectrum for melanin-specific selective photothermolysis," Lasers in Surgery and Medicine, vol. 9, pp. 389-397, 1989.

J.A. Parrish, "Selective thermal effects with pulsed irradiation from lasers: From organ to organelle," Journal of Investigative Dermatology, vol. 80, No. 6 Supplement, pp. 75s-80s, 1983.

L. Polla et al., "Melanosomes are a primary target of Q-switched ruby laser irradiation in guinea pig skin," Journal of Investigative Dermatology, vol. 89, No. 3, pp. 281-286, Sep. 1987.

T. Shimbashi & T. Kojima, "Ruby laser treatment of pigmented skin lesions," Aesth. Plast. Surg., vol. 19, pp. 225-229, 1995.

Stratton, K., et al., "Biological Effects of Laser Radiation II: ESR Studies of Melanin Containing Tissues after Laser Irradiation," Northeast Electronics Research and Engineering Meeting—NEREM Record, IEEE Catalogue No. F-60, pp. 150-151, Nov. 1965.

C.R. Taylor et al., "Treatment of tattoos by Q-switched ruby laser," Arch. Dermatol. vol. 126, pp. 893-899, Jul. 1990.

V.V. Tuchin, "Laser light scattering in biomedical diagnostics and therapy," Journal of Laser Applications, vol. 5, No. 2-3, pp. 43-60, 1993.

S. Watanabe et al, "Comparative studies of femtosecond to microsecond laser pulses on selective pigmented cell injury in skin," Photochemistry and Photobiology, vol. 53, No. 6, pp. 757-762, 1991.

A.J. Welch et al., "Evaluation of cooling techniques for the protection of the pidermis during HD-yag laser irradiation of the skin," Neodymium-Yag Laser in Medicine and Surgery, Elsevier Science Publishing Co., publisher, pp. 195-204, 1983.

R.B. Yules et al., "The effect of Q-switched ruby laser radiation on dermal tattoo pigment in man," Arch Surg, vol. 95, pp. 179-180, Aug. 1967.

E. Zeitler and M. L. Wolbarsht, "Laser Characteristics that Might be Useful in Biology," Laser Applications in Medicine and Biology, vol. I, M.L. Wolbarsht, editor, Plenum Press, publishers, Chapter 1, pp. 1-18, 1971.

Abstracts Nos. 17-19, Lasers in Surgery and Medicine, ASLMS, Supplement 13, 2001.

Abstracts Nos. 219-223, ASLMS.

Abstracts, various.

Invention description to certificate of authorship, No. 532304, "The way of investigation of radiation time structure of optical quantum generator".

Invention description to certificate of authorship, No. 719439, "The ring resonator of optical quantum generator".

Invention description to certificate of authorship, No. 741747, "The modulator of optical radiation intensity".

Invention description to certificate of authorship, No. SU 1257475 A1, "Laser interferometric device to determine no-linearity of an index of refraction of optical medium".

Invention description to certificate of authorship, No. SU 1326962 A1, "The way of determination of non-linearity of an index of refraction of optical medium".

* cited by examiner

METHOD AND APPARATUS FOR LASER REMOVAL OF HAIR

REFERENCE TO RELATED APPLICATIONS

This application is a continuation-in-part of U.S. application Ser. No. 09/394,171 filed Sep. 13, 1999, now U.S. Pat. No. 6,514,242 B1, by the present inventor David B. Vasily and his then co-inventor Peter L. Dorogi, which claims the benefit of Provisional Application Ser. No. 60/110,732, filed Dec. 3, 1998.

BACKGROUND OF THE INVENTION

1. Field of the Invention

This invention relates to the field of laser dermatology and more particularly concerns a method and apparatus for removing hair from living skin while minimizing irritation or injury to the skin.

2. The Related Art

Location, location, location. Just as in real estate, the beauty of hair is where it rises. A forest of hair on the scalp is considered a blessing. On the upper lip it may be less desirable, most especially less desirable for females. Location on the legs is deemed also not at all attractive.

Removal of unwanted hair is commonly achieved by shaving for short-term results. Mechanical epilation with wax or other devices provides a longer respite. Several disadvantages accompany these methods. Frequently they cause irritation, folliculitis and on rare occasions scarring. There are presently several FDA-approved treatments for hair removal. Electrolysis involves resistive heating around an electrode placed deeply into a hair follicle, causing complete or partial destruction of such follicle. Such treatment is painful, tedious and only moderately effective. About 50 to 85% of treated hairs, furthermore, re-grow. There are also significant risk effects here of folliculitis and infection.

Another FDA-cleared treatment (Thermolase technique) involves exposure to a Q-switched Nd:YAG laser designed for tattoo removal, following wax epilation and topical application of a suspension of amorphous carbon particles. This treatment is mildly painful. Despite aggressive marketing, its effectiveness appears to be minimal or nonexistent. The potential complications of this treatment are those of laser surgery in general (infection, scarring, pigmentary changes), plus the risk of inadvertent tattooing by introducing carbon into the dermis through ruptured follicles. However, these complications presumably occur at an acceptably low incidence.

A safer and more effective system has been described by Dr. Rox Anderson of the Harvard Medical School and commercialized by Palomar Corporation. The system uses a ruby laser with light delivered through a transparent actively-cooled sapphire hand piece held directly in contact with the skin. The hand piece conducts heat away from the epidermis before, during and after each pulse.

Transient inflammatory reaction (erythema, edema) and pigmentary changes (hypopigmentation, hyperpigmentation) are routine and expected whenever a laser is used to injure some component of the skin. Compared with pulsed dye, Q-switched and other lasers used for cosmetic procedures, the Palomar laser produces similar skin injury followed by rapid healing requiring minimal wound care. Compared with electrolysis, in which bacteria are frequently repeatedly introduced into follicles from the skin surface by a needle-like electrode, the laser system may cause less folliculitis. Nonetheless, it is very evident there is a need for much safer procedures to avoid skin damage and to also minimize the number of treatments required for effective hair removal.

Patent References

In addition to the above general prior art, applicant is familiar with the following prior art patents of interest.

U.S. Pat. No. 5,671,735 issued to MacFarlane et al. on Sep. 30, 1997 discloses broadly the use of a colorimeter in the diagnosis of medical conditions. MacFarlane's technique involves basically the taking of a preliminary colorimeter reading of the skin before a disease condition occurs, storing this for reference in an associated computer and then later taking another reading to see if a skin color change has occurred, which, if present, may indicate a disease condition has occurred. Later readings may be used to monitor recovery. Various color instruments are disclosed. A later MacFarlane et al. U.S. Pat. No. 6,308,088 issued Oct. 23, 2001 includes expanded tables of colors including extensive hair color tables.

U.S. Pat. No. 6,015,404 issued to Altshuler et al. on Jan. 18, 2000 includes the use radiation type temperature detection devices to monitor the use of a dermatology laser device.

U.S. Pat. No. 6,050,990 issued to Tankovich et al. on Apr. 18, 2000 includes a comprehensive discussion of the use of lasers for various skin treatment purposes, including, in particular, the removal of hair, or depilation. Tankovich et al. teaches that the laser beam can be adjusted in terms of wave length, fluence, pulse repetition rate and pulse duration and that it should be adjusted in accordance with the type and condition of the patient's skin and hair. Information concerning these is to be obtained by the use of a set of questions including the color of the skin and hair and the possible use of photography to document the answers. Tankovich does not teach or even mention the use of a calorimeter to aid in determining the settings or treatment with the laser.

U.S. Pat. No. 6,149,644 issued to Xie on Nov. 21, 2000 discloses a method of treating the skin by actinic light, i.e. light sufficient to form a chemical change or induce photochemical activity, one use being hair removal. Xie discloses broadly that skin is less effected by light in the 600 to 999 nm range than hair follicles. In order to decrease the light to any specific portion of skin Xie continuously moves his light beam, whether continuous or pulsed as in a laser, along narrow contiguous paths thereby reducing the amount of energy applied to any specific spot while fully covering over a discrete period a full area.

U.S. Pat. No. 6,168,589 to Tobinick which contains a good description of the state of the art of laser depilation of the skin at the time of Applicants' filing date and suggests that the treatment should be customized according to the skin color, hair color, hair diameter and anatomy of the particular site being treated and points out that dark skinned persons and light skin persons must be treated differently as darker skin are more easily burned. Tobinick's particular solution was to divide patients into groups or categories of darkness of skin and coarseness and darkness of hair, determine the "thermal relaxation time," i.e. the time for a uniform amount of heat to diffuse from a volume of material and adjust his laser pulses in pulse sequence time so as not to exceed the thermal relaxation time of the structure or the structures to be destroyed or damaged, i.e. the hair follicle, but to exceed the thermal relaxation time of the structures that are desired not to be damaged. There is no disclosure whatsoever of the use of a colorimeter.

U.S. Pat. No. 6,251,100 to Flock et al. teaches the use of lasers to perforate the epidermis pursuant to the application of topical anesthetics and the like to and through the skin in place of an injection. The aim is to perforate the skin with as little damage as possible. Flock sets forth a number of examples and in example 12 used a colorimeter to detect erythema or reddening of the skin as a sign of skin damage or irritation. Flock discloses the use of laser beams for other treatments as well, including, in example 17, the removal of nose hairs, but there is no disclosure of the use of a calorimeter to monitor the results.

Non-Patent References

1. Fitzpatrick T. The validity and practicality of sun-reactive skin types I–VI. Arch Dermatol 1988; 124:869–871.
2. Nanni C A, Alster T S. Laser-assisted hair removal: side effects of Q-switched Nd:YAG, long-pulse diode and alexandrite lasers. J Am Acad Dermatol 1999; 41:167–171.
3. Takimaki, H. Measurement of skin color: practical application and theoretical consideration. The J of Med Invest 1998; 44:121–125.
4. Fullerton A, Fischer T. Laht; et al. Guidelines for measurement of skin color and erythema. Contact Dermatitis 1995; 35:1–10.

OBJECTS OF THE INVENTION

Accordingly, it is an object of the present invention to provide a method for epilation which minimizes transient inflammatory reactions and pigmentary changes. It is a still further object of the invention to provide a method of depiliation or epilation of the skin which prevents any accompanying injury to the skin.

It is a object of the present invention is to provide an epilation method based on laser energy levels or doses which minimize the number of treatments necessary to effect full epilation.

It is a still further object of the invention to provide a simple easily determined reading of skin color using particular ranges of remitted light that provide a reliable indication for a physician or technician of the laser energy to be used in depilation of the skin of various patients without injury to the skin.

It is a still further object of the invention to provide a method of depilation using the green and blue remittance of light from the skin to make reading which can be altered to an accurate calculation of the energy to be fed to a laser for depilation of the epidermis without injury.

These and other objects of the present invention will become more apparent from the following summary and detailed description.

SUMMARY OF THE INVENTION

Prior to treatment with a laser to incapacitate the hair follicles in order to effect depilation of the skin, the area of the skin to be treated is read with a colorimeter adapted to obtain readings respecting the amount of remittent light in the green and blue range and these readings are used in a previously validated mathematical formula to provide a therapeutic dosage of laser light effective to inactivate hair follicles in the skin area. Normally the so-called L.a.b. calorimeter system using the b/L relationship will be used. However, any equivalent system measuring light in the green and blue range may be used such as the related X, Y, Z color coordinates with a suitable previously validated formula to provide equivalent laser light dosages.

DESCRIPTION OF THE PREFERRED EMBODIMENTS

The following detailed description is of the best mode or modes of the invention presently contemplated. Such description is not intended to be understood in a limiting sense, but to be an example of the invention presented solely for illustration thereof, and by reference to which in connection with the following description and the accompanying drawings one skilled in the art may be advised of the advantages and construction of the invention.

Human skin color is extremely difficult to characterize accurately by clinical observation alone. In general, in light skin, containing very little or minimal melanin, the primary light absorbing chromophore is hemoglobin. Absorption of incident green light by hemoglobin results in reddish skin colors, whereas absorption of blue light by more melanized skin results in a green-red blend, with the resultant appearance of browner tones of skin. In addition, identical skin tones under one light can appear very different under a different light. This varying color, or so-called metamerism, renders it essentially impossible to consistently and/or accurately characterize the true color of skin. Human skin is metameric due to variable optical properties of epidermal melanin.

In earlier times ruby laser dosimetry was based on so-called Fitzpatrick skin types. This typing, which predicts ability to melanize, rather than degree of melanization, was found to be unreliable and patients so treated experienced an unacceptably high incidence of tissue complications, including crusting, blistering, and pigmentary changes. In some instances, pigmentary changes such as hypopigmentation were long-lasting and took as much as up to one year to resolve.

In an effort to develop a better and more reliable quantitative method for determining proper dosimetry that would allow reproducible complication-free and highly effective laser hair removal in a high percentage of patients, the present inventor tried to correlate the readings of a reflectance spectrophotometer to determine the color of the skin of potential patients and to correlate this with the results of subsequent laser treatment.

Reflectance spectrophotometry is based on the principle of the measurement of an object's spectral reflectance, determined after illumination with a uniform amount of delivered light from a visible light source. The reflected light from the object typically passes through spectral sensors and microcomputers that calculate and assign numerical values L* a* b* to an object. These values are algebraic expressions of the XYZ tristimulus values, defined by the CIE (Commission International de l'Eclairage) in 1931, to characterize an object's color with X (red), Y (green) and Z (blue) spectrum values.

The L* a* b* color space is a commonly used source for quantitating color data. Defined by the CIE 1976, this space or system was designed to provide uniform values corresponding to or allowing for differences in human visual perception. The L* in this space or system indicates lightness, the a* the+(red),–(green) direction and b* the+(yellow)–(blue) directions.

At first a handheld reflectance spectrophotometer to determine various reading, initially, b* readings only was experimented with and, subsequently after more experimentation and correlation's, the b*/L* ratio was concentrated upon. Ultimately it was determined that this was the value that correlated most closely with the melanin content of skin.

The b/L ratio was found to be highly predictive of melanin content of human skin since it localizes color readings to the brown area of the color sphere. This ratio, after extensive experimentation, showed a strong linear correlation with effective, safe laser doses.

It has been discovered, therefore, that laser-based removal of hair can be rendered more effective while less irritating through guidance by skin coloration type in selecting the most efficient laser energy dosage. Colorimetry values obtained from a spectrophotometer can, therefore, with proper correlation now guide selection of the optimal laser energy.

According to a first step of the method of this invention, skin color is analyzed by a spectrophotometer/colorimeter. These instruments usually operate with at least one visible light source such as a light emitting diode (LED), xenon-arc, tungsten/halogen or other light source in the wavelength range of 400 to 900 nm. The visible light source may be co-housed with the sensor portion of the spectrophotometer/colorimeter. Both visible and infrared wavelength light may be utilized in connection with a sensor portion. A suitable hand-held instrument is commercially available from Minolta Camera Company Ltd., Japan (Minolta Spectrophotometer/colorimeter CM-2002), from Colortec Associates, Accuracy Measurements Inc. and X-Rite.

Skin coloration can be expressed in values of lightness, redness and yellowness respectively denoted by L*, a* and b* units.

The L*a*b* color space is related to the Individual Typology Angle, which is essentially the value of 57.3 arctangent [(L*−50)b*], identifying skin types. See Chardon et al., International Journal of Cosmetic Science, 13, 191–208 (1991). Type I, the very lightest skin color, covers an angle ranging from more than 55 to 60°; Type II, light skin color, covers an angle ranging from more than 41 to 55°; Type III, intermediate skin color, covers an angle ranging from more than 28 to 41°; Type IV, tan skin color, covers an angle ranging from more than 10 to 28°; and Type V, brown skin color, covers an angle ranging from 0 to 10°.

Individual Typology Angle correlates to a first approximation with visibly judged Skin Type and to a first approximation determines the correct laser setting. However, visual judgement of Skin Type may also be influenced by optical contributions from hemoglobin as well as that of melanin. A second shortcoming of the currently practiced art of Skin Typing is the phenomenon called metamerism, in which two skin colors that appear the same to the human eye under one light source are seen to be different under other lighting conditions. Human skin is metameric because people of different ethnic origins can have different optical types of melanin in their skin. The calorimeter used in the present method is designed to provide L*a*b* values that are the best metameric fit (average) for fluorescent lighting, daylight and incandescent light. Since the ruby laser interacts selectively with melanin, the primary optical parameters to be chosen must be those most sensitive to skin melanin content for more accurate selections of laser dosage for epilation.

The melanin absorption of incident light has a lower amplitude for lighter skin and a greater amplitude for darker skin, respectively. In the former case the skin color spectrum is partly domated by hemoglobin absorbance, in the latter case by melanin absorbance. For lighter skin (low melanin), the absorbance of primarily green light by hemoglobin imparts a reddish remittance to the skin. For darker skin (high melanin content), the strong absorbance of blue light imparts a green-red combination to the remittance, giving skin a brownish color. For Caucasian skin, Types I–III, a change in melanin has a greater impact on total blue remittance than on green remittance, where hemoglobin dominates. It would appear that the best indicator of differences in skin melanin content is an optical parameter that compares remittance intensities in the blue part of the spectrum (heavily reduced by melanin absorbance) against the green remittance (heavily reduced by hemoglobin absorbance). Consequently, for Skin Types I–IV, one can treat the green band remittance as a melanin-independent baseline against which differences in blue-band remittance indicate differences in skin melanin content.

The standard definition of color was set in 1931 with the definition of three types of standard remitted spectra, X, Y and Z. Approximately, X is a red remittance spectrum, Y is a green spectrum, and Z is a blue spectrum. The psychological color perception parameters L*a*b* are actually algebraic transformations of X, Y, Z that accommodate the human mind's relative sensitivities to the X-, Y- and Z-spectra:

$$L^* = 116(Y/Y_a)^{1/2} - 16$$

$$a^* = 500[(X/X_a)^{1/3} - (YY_a)^{1/3}]$$

$$b^* = 200[(Y/Y_a)^{1/3} - (Z/Z_a)^{1/3}]$$

where $X_a$, $Y_a$, and $Z_a$ are maximum values of the remittance for the particular illumination intensity. Looking at these three definitions reveals that the quantity b* compares blue to green remittance, Z versus Y, which is the object of the present method.

Table I shows the range of Skin Types for sixty-seven panelists in a clinical study performed for the present invention. Data correlation between the measured angle and the Skin Type subjectively assigned in the study is weak, pointing out the inferiority of the known Skin Typing method.

TABLE I

| PATIENT | SKIN TYPE | (ARC TAN) ( (L-50)/B) ) |
|---|---|---|
| 1 | II | 33.44 |
| 2 | III | 36.19 |
| 3 | III | 44.41 |
| 4 | II | 52.12 |
| 5 | I | 41.92 |
| 6 | II | 32.35 |
| 7 | III | 45.00 |
| 8 | II | 54.29 |
| 9 | III | 43.78 |
| 10 | III | 55.25 |
| 11 | II | 35.51 |
| 12 | II | 37.37 |
| 13 | II | 40.68 |
| 14 | II | 44.63 |
| 15 | IV | 20.24 |
| 16 | II | 50.37 |
| 17 | III | 33.85 |
| 18 | III | 28.79 |
| 19 | II | 50.07 |

TABLE I-continued

| PATIENT | SKIN TYPE | (ARC TAN) ( (L-50)/B) ) |
|---|---|---|
| 20 | II | 23.92 |
| 21 | III | 58.20 |
| 22 | III | 22.85 |
| 23 | II | 34.80 |
| 24 | III | 37.54 |
| 25 | III | 48.45 |
| 26 | III | 51.51 |
| 27 | III | 43.15 |
| 28 | III | 60.96 |
| 29 | II | 48.57 |
| 30 | II | 41.13 |
| 31 | III | 33.38 |
| 32 | III | 41.36 |
| 33 | III | 24.25 |
| 34 | I | 38.63 |
| 35 | IV | 29.06 |
| 36 | I | 52.86 |
| 37 | I | 58.44 |
| 38 | II | 47.78 |
| 39 | III | 35.86 |
| 40 | I | 53.92 |
| 41 | III | 22.80 |
| 42 | V | 6.98 |
| 43 | IV | 31.88 |
| 44 | II | 36.67 |
| 45 | II | 28.28 |
| 46 | I | 59.56 |
| 47 | II | 54.52 |
| 48 | III | 49.43 |
| 49 | I | 60.54 |
| 50 | II | 52.97 |
| 51 | II | 51.50 |
| 52 | II | 51.63 |
| 53 | II | 52.14 |
| 54 | II | 31.94 |
| 55 | II | 51.17 |
| 56 | IV | 38.13 |
| 57 | — | 37.91 |
| 58 | IV | 35.60 |
| 59 | II | 46.49 |
| 60 | III | 49.52 |
| 61 | — | 48.53 |
| 62 | III | 31.05 |
| 63 | III | 25.52 |
| 64 | III | 44.20 |
| 65 | III | 41.45 |
| 66 | II | 63.19 |
| 67 | II | 33.58 |

TABLE II

L*a*b* (Laser Dose J/cm²)

| PATIENT | SKIN TYPE | L* | a* | b* | LASER DOSE (J/cm²) |
|---|---|---|---|---|---|
| 1 | II | 60.26 | 11.94 | 15.54 | 18 |
| 2 | III | 60.74 | 14.72 | 14.68 | 21 |
| 3 | III | 65.40 | 6.10 | 15.72 | 18 |
| 4 | II | 66.84 | 6.68 | 13.10 | 20 |
| 5 | I | 64.22 | 8.80 | 15.84 | 17 |
| 6 | II | 60.88 | 13.04 | 17.18 | 12 |
| 7 | III | 64.80 | 8.70 | 14.80 | 18 |
| 8 | II | 69.58 | 5.70 | 14.08 | 18 |
| 9 | III | 64.68 | 9.88 | 15.32 | 16 |
| 10 | III | 72.92 | 4.70 | 15.90 | 19 |
| 11 | II | 61.15 | 14.68 | 15.63 | 16 |
| 12 | II | 61.96 | 11.10 | 15.66 | 18 |
| 13 | II | 63.70 | 10.06 | 15.94 | 16 |
| 14 | II | 60.80 | 14.20 | 10.94 | 20 |
| 15 | IV | 56.86 | 11.54 | 18.12 | 10 |
| 16 | II | 66.66 | 10.64 | 13.80 | 18 |
| 17 | III | 61.28 | 12.04 | 16.82 | 15 |
| 18 | III | 59.22 | 11.06 | 16.78 | 12 |

TABLE II-continued

L*a*b* (Laser Dose J/cm²)

| PATIENT | SKIN TYPE | L* | a* | b* | LASER DOSE (J/cm²) |
|---|---|---|---|---|---|
| 19 | II | 67.05 | 7.05 | 14.28 | 18 |
| 20 | II | 56.82 | 17.42 | 15.38 | 12 |
| 21 | III | 70.06 | 4.80 | 12.44 | 18 |
| 22 | III | 56.86 | 13.78 | 16.28 | 12 |
| 23 | II | 61.16 | 12.66 | 16.06 | 18 |
| 24 | III | 62.60 | 14.90 | 16.40 | 18 |
| 25 | III | 67.60 | 8.05 | 15.60 | 18 |
| 26 | III | 67.10 | 8.35 | 13.60 | 18 |
| 27 | III | 64.23 | 10.63 | 15.18 | 18 |
| 28 | III | 71.67 | 4.23 | 12.03 | 20 |
| 29 | II | 64.66 | 9.34 | 12.94 | 18 |
| 30 | II | 62.40 | 12.50 | 14.20 | 25 |
| 31 | III | 61.30 | 11.20 | 17.15 | 18 |
| 32 | III | 64.42 | 7.70 | 16.38 | 14 |
| 33 | III | 57.62 | 14.10 | 16.92 | 12 |
| 34 | I | 62.00 | 11.30 | 15.02 | 20 |
| 35 | IV | 59390 | 11.40 | 17.82 | 20 |
| 36 | I | 64.02 | 10.80 | 10.62 | 35 |
| 37 | I | 67.45 | 7.50 | 10.72 | 35 |
| 38 | II | 62.63 | 14.13 | 11.46 | 22 |
| 39 | III | 62.65 | 11.42 | 17.50 | 25 |
| 40 | I | 67.22 | 8.07 | 12.55 | 33 |
| 41 | III | 56.62 | 15.80 | 15.75 | 15 |
| 42 | V | 52.20 | 13.86 | 17.98 | 13 |
| 43 | IV | 61.32 | 11.92 | 18.20 | 21 |
| 44 | II | 60.70 | 13.65 | 14.37 | 20 |
| 45 | II | 65.47 | 12.47 | 13.70 | 25 |
| 46 | I | 66.42 | 10.65 | 9.65 | 25 |
| 47 | II | 67.70 | 9.23 | 12.62 | 30 |
| 48 | III | 65.80 | 9.65 | 13.53 | 20 |
| 49 | I | 70.00 | 7.07 | 11.30 | 30 |
| 50 | II | 66.30 | 9.90 | 12.30 | 25 |
| 51 | II | 67.60 | 7.40 | 14.00 | 25 |
| 52 | II | 66.90 | 9.86 | 13.38 | 30 |
| 53 | II | 66.80 | 7.87 | 13.06 | 30 |
| 54 | II | 60.26 | 13.20 | 16.46 | 22 |
| 55 | II | 68.96 | 8.80 | 15.26 | 30 |
| 56 | IV | 63.50 | 9.50 | 17.20 | 25 |
| 57 | — | 61.72 | 14.25 | 15.05 | 26 |
| 58 | IV | 61.67 | 13.12 | 16.30 | 15 |
| 59 | II | 62.85 | 11.95 | 12.20 | 35 |
| 60 | III | 65.85 | 9.85 | 13.53 | 20 |
| 61 | — | 68.80 | 5.82 | 16.62 | 30 |
| 62 | III | 58.97 | 16.12 | 14.90 | 22 |
| 63 | III | 57.70 | 16.06 | 16.13 | 25 |
| 64 | III | 63.37 | 14.40 | 13.75 | 20 |
| 65 | III | 63.00 | 12.58 | 14.72 | 20 |
| 66 | II | 67.15 | 4.57 | 9.68 | 25 |
| 67 | II | 57.90 | 17.45 | 11.90 | 20 |

TABLE III

| LASER DOSE (J/cm²) | b*/L | b* | a*/b* |
|---|---|---|---|
| 18 | 0.258 | 15.54 | 0.768 |
| 21 | 0.242 | 14.68 | 1.003 |
| 18 | 0.240 | 15.72 | 0.38 |
| 20 | 0.196 | 13.10 | 0.510 |
| 17 | 0.247 | 15.84 | 0.556 |
| 12 | 0.282 | 17.18 | 0.759 |
| 18 | 0.228 | 14.80 | 0.588 |
| 18 | 0.202 | 14.08 | 0.405 |
| 16 | 0.297 | 15.32 | 0.645 |
| 19 | 0.218 | 15.90 | 0.296 |
| 16 | 0.256 | 15.63 | 0.939 |
| 18 | 0.253 | 15.66 | 0.709 |
| 16 | 0.250 | 15.94 | 0.631 |
| 20 | 0.180 | 10.94 | 1.298 |
| 10 | 0.320 | 18.12 | 0.637 |
| 18 | 0.207 | 13.80 | 0.771 |

TABLE III-continued

| LASER DOSE (J/cm$^2$) | b*/L | b* | a*/b* |
|---|---|---|---|
| 15 | 0.274 | 16.82 | 0.716 |
| 12 | 0.283 | 16.78 | 0.659 |
| 18 | 0.213 | 14.28 | 0.494 |
| 12 | 0.271 | 15.38 | 1.133 |
| 18 | 0.178 | 12.44 | 0.386 |
| 12 | 0.286 | 16.28 | 0.846 |
| 18 | 0.263 | 16.06 | 0.788 |
| 18 | 0.222 | 16.40 | 0.909 |
| 18 | 0.231 | 15.60 | 0.516 |
| 18 | 0.203 | 13.60 | 0.614 |
| 18 | 0.236 | 15.18 | 0.700 |
| 20 | 0.168 | 12.03 | 0.352 |
| 18 | 0.200 | 12.94 | 0.722 |
| 25 | 0.228 | 14.20 | 0.880 |
| 18 | 0.280 | 17.15 | 0.653 |
| 14 | 0.254 | 16.38 | 0.470 |
| 12 | 0.294 | 16.92 | 0.833 |
| 20 | 0.242 | 15.02 | 0.752 |
| 20 | 0.297 | 17.82 | 0.640 |
| 35 | 0.166 | 10.62 | 1.017 |
| 35 | 0.159 | 10.72 | 0.700 |
| 22 | 0.183 | 11.46 | 1.233 |
| 25 | 0.279 | 17.50 | 0.653 |
| 33 | 0.187 | 12.55 | 0.643 |
| 15 | 0.278 | 15.75 | 1.003 |
| 13 | 0.344 | 17.98 | 0.771 |
| 21 | 0.297 | 18.20 | 0.655 |
| 20 | 0.237 | 14.37 | 0.950 |
| 25 | 0.209 | 13.70 | 0.910 |
| 25 | 0.145 | 9.65 | 1.104 |
| 30 | 0.186 | 12.62 | 0.731 |
| 20 | 0.206 | 13.53 | 0.713 |
| 30 | 0.161 | 11.30 | 0.626 |
| 25 | 0.186 | 12.30 | 0.805 |
| 25 | 0.207 | 14.00 | 0.529 |
| 30 | 0.200 | 13.38 | 0.737 |
| 30 | 0.196 | 13.06 | 0.603 |
| 22 | 0.273 | 16.46 | 0.802 |
| 30 | 0.221 | 15.26 | 0.577 |
| 25 | 0.271 | 17.20 | 0.522 |
| 26 | 0.244 | 15.05 | 0.947 |
| 15 | 0.264 | 16.30 | 0.805 |
| 35 | 0.194 | 12.20 | 0.980 |
| 20 | 0.205 | 13.53 | 0.728 |
| 30 | 0.242 | 16.62 | 0.350 |
| 22 | 0.253 | 14.90 | 1.082 |
| 25 | 0.280 | 16.13 | 0.996 |
| 20 | 0.217 | 13.75 | 1.047 |
| 20 | 0.234 | 14.72 | 0.588 |
| 25 | 0.140 | 9.68 | 0.472 |
| 20 | 0.206 | 11.90 | 1.466 |

A stronger determinant of the correct Laser Dose is the ratio of Z/Y, which is derivable from the ratio of b*/L*, as can be seen from the above-shown algebraic relations. Table II shows the range of colorimetric values for skin sites from 67 individuals. These data have since the original experiments been extended to additional patients Table III shows the range of values for the Laser Dose versus b*, b*/L* and (for an arbitrary comparison) a*/b*. There is a strong linear correlation between laser dose and b* or b*/L* which can be seen when the values are graphed. In contrast, a*/b*, which is dominated by the X coordinate rather than the interrelationship of Z and Y, has a very poor correlation with Laser Dose.

Based on the calculation of statistical correlation coefficients ($R^2$), the strongest correlation with the correct Laser Dose was found for b*/L*. A linear fit to the data gives the mathematical expression for the Fluence (Laser Dose) in joules/cm$^2$ as Laser Dose=39–84(b*/L*)

The correlation's L* versus Laser Dose and a* versus Laser Dose were found to be weaker. This is expected since both L* and a* are independent of z and hence less sensitive to melanin.

Changes in the type of laser employed, cooling head configuration applied at the interface between skin and laser energy and temperature, as well as other physical factors may lead to different constants. Therefore the Laser Dose is best described by an overall general equation of the following type:

Laser Dose=$k^1$-$k^2$(b*/L*)

Where $k^1$ ranges from 1 to 60, preferably from 25 to 50, optimally form 30 to 40; and $k^2$ ranges from 1 to 120 preferably from 10 to 110, more preferably from 50 to 100, optimally from 55 to 85.

Any of the concepts and theories as well as the mathematical correlation of this invention should not be considered as limiting the actual invention itself. Adjustments to the theory may be deemed appropriate in the future but this will not negate the underlying discovery of using specific colorimetric parameters to determine the optimum laser energy dosage added for hair removal.

For purposes of this invention, most preferred is a ruby laser with output wavelength of 694 nm. Other types of lasers may also be employed. These include carbon dioxide based lasers and Q-switched Nd:YAG lasers pulsed at 1064 nm. Particularly useful may be an Alexandrite laser operating at 755 nm, a typical commercial instrument being the Gentle LASE available from Candela Corporation, Wayland, Mass. A still further potentially useful laser is the KTP Crystal Diode type emitting at 810 nm, available from Coherent Corporation.

Advantageously, probes of lasers according to the present invention may include a cooling head. Temperatures ranging from 0° C. down to minus 80° C., preferably between 0° C. and minus 10° C. are employed for this invention. For instance, the Palomar Ruby Laser 2000 model operates at minus 10° C. utilizing a Thermatech Pump with a sapphire tip. A TFE cryogen sprayhead may also be employed and is commercially available with the Gentle Las instrument from Candela Corporation.

Pulse duration is best when extended but only to the point falling short of skin damage. With the Palomar Ruby Laser (Epiwand instrument), there is a fixed duration of 3 milliseconds for each pulse. Generally pulse duration may range from about 0.5 to about 10 milliseconds.

For patients who are tanning or have tanned skin, and b/L ratios greater than 0.250 it is preferred to use the SLP810™ diode, not only to prevent tissue complications due to reduced melanin absorption at this wavelength, but because tissue tolerated ruby laser fluences for patients with b/L ratios greater than 0.250 are simply not adequate to achieve predictable and lasting permanent hair reduction. The use of the SLP810™ diode overcomes this problem and allow these tan patients to be treated with fluences necessary to prevent hair growth.

A first embodiment of equipment for purposes of this invention includes a spectrophotometer/colorimeter physically separate from the laser. Information gathered from L*a*b* measurement or color matching of skin type is utilized to adjust laser dose levels. Input to the laser on dosage may either be through manual adjustment or automatic by electronic transfer. Skin color values can be sent to a computer program which then automatically sets energy dosage in the laser. A second embodiment of equipment for purposes of this invention combines in a single instrument the spectrophotometer/colorimeter and laser. Circuitry and a logic chip allows color values to be measured and dosage level set in a seamless, fully automatic mode.

Figure 1:
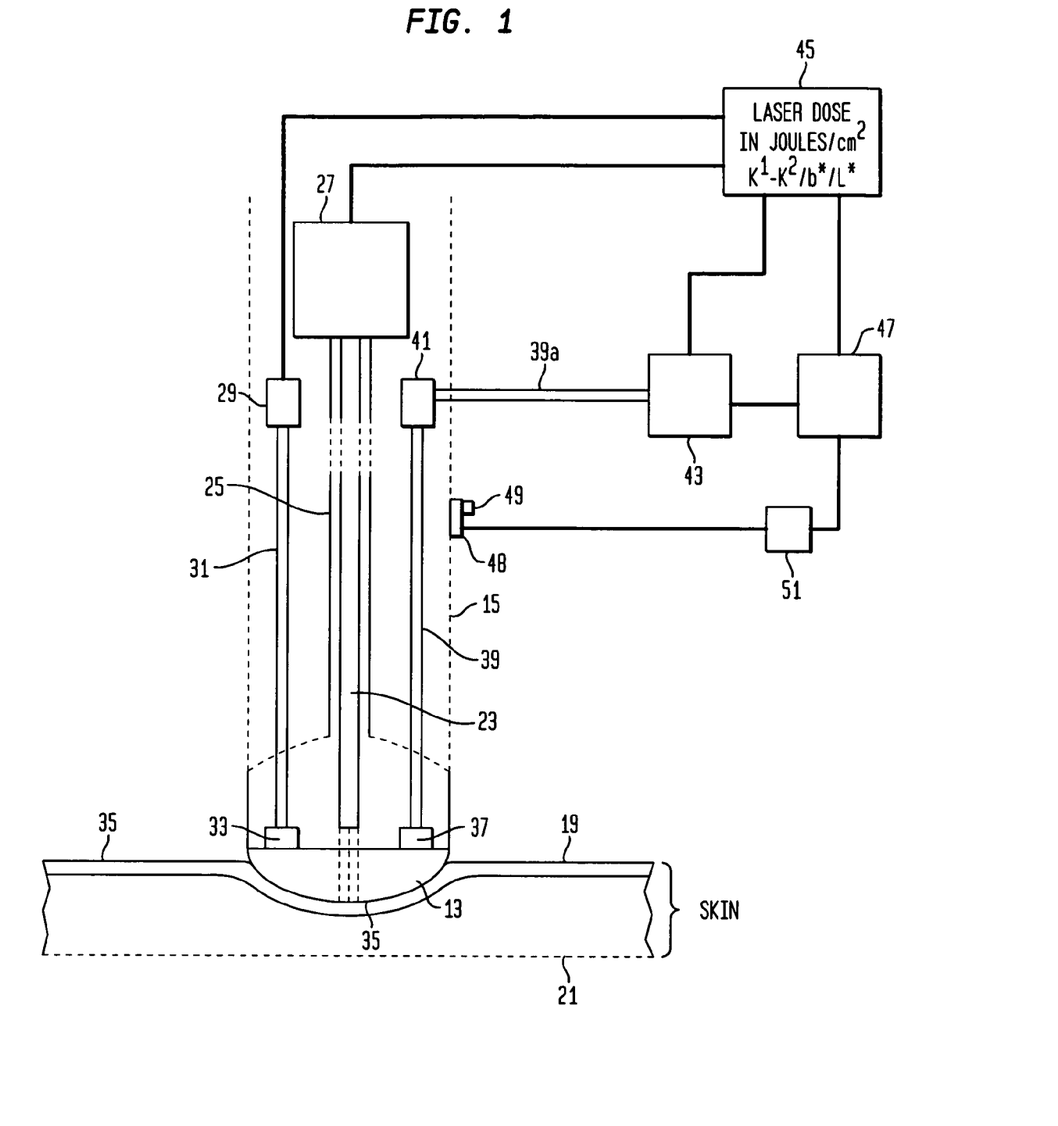
FIG. 1 is a diagrammatic block diagram type depiction of one possible embodiment of a combined apparatus for practicing the invention.

FIG. 1 is a diagrammatic illustration of one possible embodiment of a combination of a calorimeter and laser designed particularly for depilation or epilation of the skin, plus a coordination and control system for practicing the invention. In FIG. 1 there is shown in diagrammatic form a laser apparatus 11 having a lens 13 at the lower end of a wand 15, shown here in broken lines to indicate the surface of said wand, which is adapted to be held in the hand, not shown, of an operator with the terminal lens 13 against the skin of a patient, such skin being indicated by reference numeral 17. Reference numeral 19 designates the outer layer of skin, or the epidermis, and 21 designates the middle layer of skin, or dermis, in which the various major components of the skin such as the hair follicles sebaceous glands minor blood vessels and the like are found. Melanin, the main coloring matter and light protective element in the skin is found mostly in the upper layer of the dermis, in the epidermis, which is principally a layer of dead outer cells, and around the hair follicles in the dermis. As shown, the lens 13 is pressed against the skin indenting the epidermis plus the upper portion of the dermis. A fiberoptic light transmission element 23 is contained in a suitable sheathing 25, which extends from a laser light generator 27 to the lens 13, which lens is diagrammatically indicated oversize to better illustrate how it can compress the upper layers of skin when in use and also how an illuminating light source 29 may conduct light preferably of a midrange light in the wavelength range of 400 to 900 nm through a second fiberoptic transmission element 31 and transmit it through transparent connecting element 33 to the lens 13, which transmits said light to the skin surface or surface 35 of the epidermis 19. Reflected or remitted light from such skin surface 35 or intersection of the epidermis 19 and lens 13 will be then transmitted to interconnecting element 37 on the opposite side of the top of the lens 13 and through fiberoptic transmitter 39 to coupling or transmitter 41 which transfers either such light or its analog in the form of another electromagnetic signal to colorimeter 43, which detects at least the intensity of remittent green and red light and directs such information to computer 45, which will convert the calorimetric indication through a suitable algorithm set forth above to a pulse dosage signal for the laser 27. A timing device 47 provides suitable signals to coordinate signals from arming switch 48 upon the operator initiating a treatment cycle by pressing the lens 13 of the wand 15 against the epidermis 19 of a patient and pressing the activator button 49. This activates illuminating light source 29 through suitable computer circuits which light source directs a light beam through fiberoptic transmission element 31 to the lens 13 where it illuminates the surface of the epidermis 19. Reflected light, or remittance light, from such skin surface is then picked up by element 37 and is transmitted through fiberoptic element 39 to colorimeter apparatus 43 where it is separated into its component wave lengths and the blue and green wave lengths or components measured and directed as discrete signals to computer 45 which will calculate the laser signal to be provided by laser 27 and direct such signal, which will have been calibrated for the correct intensity and time. The sequence timer 51 will be set to determine if an initial analysis light beam will be directed at the patient and analyzed followed by as many laser pulses to the same or adjacent portions of the epidermis (directed usually at different hair follicles) or whether a complete light analysis cycle followed by a single laser pulse will be provided for each activation of the button or switch 49. As explained above, the use of a colorimeter to analyze the skin characteristics has been found to be extremely effective and efficient in analyzing the skin type either using separate colorimeter and laser apparatus or combined apparatus if the dosage of laser light is calculated in accordance with the invention based upon the blue and green remitted light which it has been found by careful validation are the most predictive wave lengths for calculating the correct laser dosage which will inactivate hair follicles with minimum incidental damage to other portions of the skin.

While it is preferred to use a colorimeter which operates in accordance with the L* a* b* system which was originally designed to provide data representative so far as possible of the true appearance of colors, it will be evident that once the proper dosage of laser light is calculated correctly in the L* a* b* system that the same dosage can be accurately calculated also in the X, Y, Z coordinate system, since the L* a* b* system is actually an algebraic transformation of the X, Y, Z coordinates designed to accommodate the human eyes relative sensitiveness to X-, Y- and Z- spectra. Where the human eye does not enter into a calculation, however, once a correlation or validation is made between the amount of blue and green remitted light in which the green band remittance acts as a melanin independent baseline against which differences in blue-based remittance effectively indicates differences in the melanin content in the skin. Once it is known, therefore, that these two remittance values are the important ones and the validation of the dosage calculation using the green and blue remittance has been conducted to determine the proper dosage of laser light based upon such green and blue remittance a different system can be shifted to based upon the same data. In short, advantage of the present invention can be taken using any comparable calculation of a similar laser dosage based upon measurement of green and blue remittance based upon or calculated from the validating data or similar data of the present inventor or original inventors.

Except in the operating and comparative examples, or where otherwise explicitly indicated, all numbers in this description indicating amounts of material ought to be understood as modified by the word "about."

The foregoing description illustrates selected embodiments of the present invention. In light thereof variations and modifications will be suggested to one skilled in the art, all of which are within the spirit and purview and this invention. Consequently, while the present invention on has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

I claim:

1. A system for using a laser to depilate the skin comprising:
    (a) an illumination source for the skin,
    (b) an apparatus for determining blue and green remittance values from illuminated skin,
    (c) computer apparatus adapted for converting the blue and green remittance values to a signal in accordance with a previously validated algorithm, such that the signal correlates to an optimum numerical range of laser dosage energy to deactivate hair follicles with minimum damage to the skin, and (d) a laser to which said computer apparatus directs said signal.

2. A system in accordance with claim 1 in which the computer apparatus is arranged to calculate the laser dose in accordance with the formula:

$$\text{Laser Dose} = k^1 - k^2(b^*/L^*)$$

wherein $k^1$ ranges from 1 to 60 and $k^2$ range from 1 to 120.

3. A system in accordance with claim 1 making use of a ruby laser.

4. A system in accordance with claim 3 wherein the ruby laser operates at 694 nm.

5. A method of depilation of body skin comprising:
(a) illuminating a portion of the skin which is to be depilated,
(b) determining the green and blue color remittance values of such surface,
(c) expressing said remittance values in a previously validated form related to a therapeutic dosage of laser light which will deactivate hair follicles without injury to the skin tissues, and
(d) adjusting the dosage of a laser to correspond with the expressed value,
(e) applying a laser beam of the adjusted dosage to the area to be depilated.

6. A method in accordance with claim 5 wherein the illumination, determination of color remittance value, expression of remittance values and application of a laser beam are accomplished sequentially by a single apparatus.

7. A method in accordance with claim 5 wherein the illumination, determination of color remittance value, expression of the remittance values and application of a laser beam are accomplished sequentially by two or more separate apparatus components.

8. A method of depilation of body skin comprising:
(a) illuminating a portion of the skin which is to be depilated,
(b) determining the green and blue color remittance values of such surface,
(c) expressing said remittance values in a previously validated form related to a therapeutic dosage of laser light which will deactivate hair follicles without injury to the skin tissues, and
(d) adjusting the dosage of a laser to correspond with the expressed value,
(e) applying a laser beam of the adjusted dosage to the area to be depilated, wherein the illumination, determination of color remittance value, expression of the remittance values and application of a laser beam are accomplished sequentially by two or more separate apparatus components, such that the laser energy is provided in a dose in accordance with the formula:

$$\text{Laser Dose} = k^1 - k^2(b^*/L^*)$$

wherein $k^1$ ranges from 1 to 60 and $k^2$ range from 1 to 120.

* * * * *